(12) United States Patent
Oswal et al.

(10) Patent No.: US 12,095,431 B2
(45) Date of Patent: Sep. 17, 2024

(54) AC-COUPLED ELECTROCARDIOGRAM SIGNAL ACQUISITION SYSTEM WITH ENHANCED COMMON MODE REJECTION

(71) Applicant: Texas Instruments Incorporated, Dallas, TX (US)

(72) Inventors: Sandeep Oswal, Bangalore (IN); Raja Reddy Patukuri, Telangana (IN); Aravind Miriyala, Bengaluru (IN); Anand Hariraj Udupa, Karnataka (IN); Hari Babu Tippana, Bangalore (IN); Aatish Chandak, Bangalore (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 447 days.

(21) Appl. No.: 17/362,443

(22) Filed: Jun. 29, 2021

(65) Prior Publication Data

US 2022/0416741 A1 Dec. 29, 2022

(51) Int. Cl.
*H03F 3/45* (2006.01)
*A61B 5/308* (2021.01)

(52) U.S. Cl.
CPC ......... *H03F 3/45475* (2013.01); *A61B 5/308* (2021.01); *H03F 2200/165* (2013.01)

(58) Field of Classification Search
USPC ........................................................ 324/607
See application file for complete search history.

(56) References Cited

U.S. PATENT DOCUMENTS

2012/0223709 A1* 9/2012 Schillak ............ G01R 33/3621
324/309

* cited by examiner

*Primary Examiner* — Farhana A Hoque
(74) *Attorney, Agent, or Firm* — John R. Pessetto; Frank D. Cimino

(57) ABSTRACT

An ECG signal acquisition system includes a first amplifier which has a non-inverting input adapted to be coupled to a first differential input, an inverting input adapted to be coupled to a second differential input, and an output. The system includes first and second biasing resistors coupled between the non-inverting and inverting inputs of the first amplifier. The system includes an average estimation circuit which has a first input coupled to the non-inverting input of the first amplifier and a second input coupled to the inverting input of the first amplifier. The system includes a driver amplifier which has an inverting input coupled to the output of the average estimation circuit, a non-inverting input coupled to receive a reference common-mode voltage, and an output. The system includes a low-pass filter coupled between the output of the driver amplifier and the biasing resistors.

16 Claims, 2 Drawing Sheets

AC-COUPLED ELECTROCARDIOGRAM SIGNAL ACQUISITION SYSTEM WITH ENHANCED COMMON MODE REJECTION

TECHNICAL FIELD

This description relates generally to electrocardiogram signal acquisition systems.

BACKGROUND

Electrocardiogram (ECG) signals are produced by contractions of the human heart which drives electrical currents and create different potentials throughout the body. By placing electrodes on the skin, ECG signals are detected and recorded. ECG signal acquisition is non-invasive, making them valuable tools to assess how well a human heart is performing.

Because ECG signals have low amplitudes (e.g., ranging from a few hundred microvolts to a few millivolts), they are susceptible to capacitive coupling of common-mode signals from AC power lines. The common-mode signals can range from 1 to 15V and, thus, can mask the ECG signals.

The ECG signals detected by the electrodes appear as differential signals which are amplified by instrumentation amplifiers. The instrumentation amplifiers apply amplification selective to the frequency components of the ECG signals and attenuate or reject common-mode signals. The ratio of the amplification of the differential signal to the amplification of the common-mode signal is termed the common-mode rejection ratio (CMRR). For accurate recording ECG signals, a high CMRR is necessary. The CMRR is increased by increasing the input impedance of the instrumentation amplifiers. Also, the CMRR is increased by suppressing the common-mode signals by applying an active bias signal which is referred to as right leg drive (RLD) signal.

SUMMARY

In one aspect, an electrocardiogram (ECG) signal acquisition system comprises a first amplifier which has a non-inverting input adapted to be coupled to a first differential input, an inverting input adapted to be coupled to a second differential input, and an output. The system comprises first and second biasing resistors coupled between the non-inverting and inverting inputs of the first amplifier. The system comprises an average estimation circuit which has a first input coupled to the non-inverting input of the first amplifier and a second input coupled to the inverting input of the first amplifier. The average estimation circuit adds the first and second differential signals and provides an average voltage at an output. The system comprises a driver amplifier which has an inverting input coupled to the output of the average estimation circuit, a non-inverting input coupled to receive a reference common-mode voltage, and an output. The system comprises a low-pass filter coupled between the output of the driver amplifier and the first and second biasing resistors. The low-pass filter allows DC current from the output of the driver amplifier to pass through, and it applies a DC bias voltage across the non-inverting and inverting inputs of the first amplifier. The system comprises a load capacitor coupled between the output of the driver amplifier and a ground terminal.

In an additional aspect, the system comprises a first capacitor coupled between a first system input and the non-inverting input of the first amplifier, a second capacitor coupled between a second system input and the inverting input of the first amplifier, and a third capacitor coupled between the output of the driver amplifier and a second output.

In an additional aspect, the first biasing resistor has a first terminal coupled to the non-inverting input of the first amplifier, the second biasing resistor has a first terminal coupled to the inverting terminal of the first amplifier, and the first and second biasing resistors have respective second terminals coupled together.

In an additional aspect, the low-pass filter has a resistor which has a first terminal coupled to the output of the driver amplifier and a second terminal coupled to the second terminals of the biasing resistors. The low pass filter has a capacitor which has a first terminal coupled to the second terminals of the biasing resistors and a second terminal coupled to a ground terminal.

In an additional aspect, an ECG signal acquisition system comprises a first system input adapted to be coupled to a first ECG input and a second system input adapted to be coupled to a second ECG input. The system comprises a first amplifier which has a non-inverting input, an inverting input, and an output. The system comprises a first capacitor coupled between the first system input and the non-inverting input of the first amplifier, and a second capacitor coupled between the second system input and the inverting input of the first amplifier. The system comprises first and second biasing resistors coupled between the non-inverting and inverting inputs of the first amplifier. The system comprises a resistor node coupled between the first and second biasing resistors. The system comprises an average estimation circuit which has a first input coupled to the non-inverting input of the first amplifier and a second input coupled to the inverting input of the first amplifier. The average estimation circuit provides an average voltage at an output. The system comprises a driver amplifier which has an inverting input coupled to the output of the average voltage estimation circuit, a non-inverting input coupled to receive a reference common-mode voltage, and an output. The system comprises a low-pass filter coupled between the output of the driver amplifier and the resistor node. The system comprises a third capacitor coupled between the output of the driver amplifier and a system output, and comprises a load capacitor coupled between the output of the driver amplifier and a ground terminal.

In an additional aspect, an ECG signal acquisition system comprises a first amplifier which has a non-inverting input adapted to be coupled to a first differential input, an inverting input adapted to be coupled to a second differential input, and an output. The system comprises first and second biasing resistors coupled between the non-inverting and inverting inputs of the first amplifier. The system comprises a resistor node coupled between the first and second biasing resistors. The system comprises an average estimation circuit which has a first input coupled to the non-inverting input of the first amplifier and a second input coupled to the inverting input of the first amplifier. The average estimation circuit adds the first and second differential signals and provides an average voltage at an output. The system comprises a driver amplifier which has an inverting input coupled to the output of the average estimation circuit, a non-inverting input coupled to receive a reference common-mode voltage, and an output. The system comprises a low-pass filter which has a first resistor coupled between the output of the driver amplifier and the resistor node, and a capacitor coupled between the resistor node and a ground terminal. The low-pass filter increases the input impedance of the first amplifier. The system comprises a load capacitor coupled between the output of the driver amplifier and a ground terminal.

BRIEF DESCRIPTION OF THE DRAWINGS

The same reference numerals or other reference designators are used in the drawings to designate the same or similar (by function and/or structure) features.

DETAILED DESCRIPTION

Figure 1:
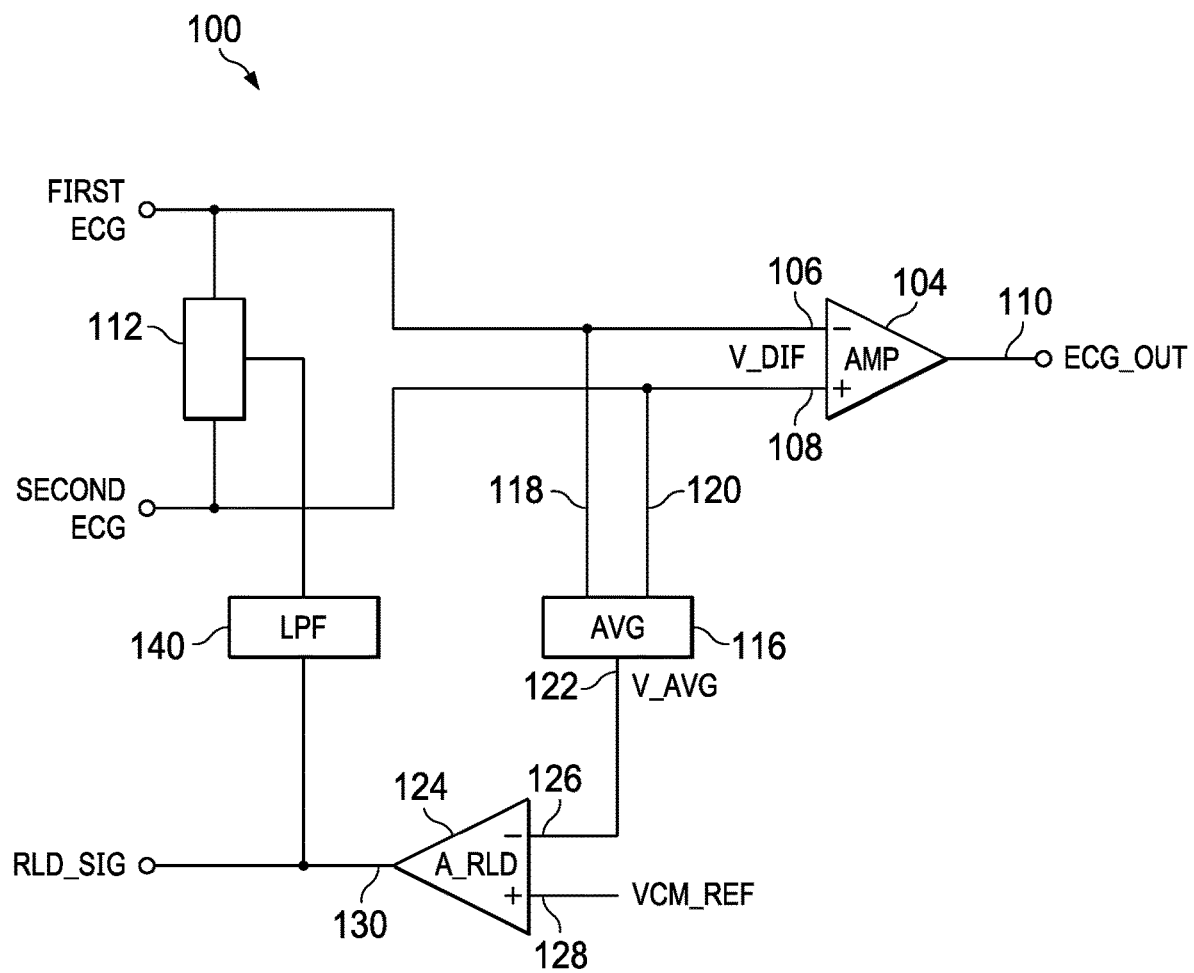
FIG. 1 is a block diagram of a system of an example embodiment.

FIG. 1 is a block diagram of an electrocardiogram (ECG) signal acquisition system 100 of an example embodiment. The system 100 includes a first amplifier 104 which has an inverting input 106 adapted to be coupled to a first differential signal (also referred to as the first ECG signal), a non-inverting input 108 adapted to be coupled to a second differential signal (also referred to as the second ECG signal), and an output 110. The first and second ECG signals appear as a differential voltage V_DIF at the inputs 106 and 108 of the first amplifier 104. The first amplifier 104 applies a gain A1 to the differential voltage V_DIF and provides an ECG output signal ECG_Out at the output 110.

The system 100 includes a biasing network 112 coupled between the non-inverting input 108 and the inverting input 106 of the first amplifier 104. As discussed below, the biasing network 112 can be formed by two resistors. Because the system 100 is an ac-coupled system, the common mode signal from a human body is not dc-coupled to the inputs 108 and 106 of the first amplifier 104. The biasing network 112 sets the common mode voltage at the inputs 108 and 106 of the amplifier 104.

The system 100 includes an average estimation circuit 116 which has a first input 118 coupled to the inverting input 106 of the first amplifier 104 and has a second input 120 coupled to the non-inverting input 108 of the first amplifier 104. As discussed below, the average estimation circuit may be implemented with an opamp. The average estimation circuit 116 adds the first and second differential signals and provides an average voltage V_AVG at an output 122. The average voltage V_AVG indicates the average of the voltage at the input 118 and the voltage at the input 120. As discussed below, a feedback loop is used to set V_AVG to be approximately equal to a reference voltage which is referred to as the common mode reference voltage VCM_REF.

The system 100 includes a driver amplifier 124 (also referred to as the right leg drive (RLD) amplifier), which has an inverting input 126 coupled to the output 122 of the average estimation circuit 116 and a non-inverting input 128 coupled to receive the reference common-mode voltage VCM_REF. The RLD amplifier 124 provides a RLD signal RLD_SIG at an output 130.

The system 100 includes a low-pass filter 140 coupled between the output 130 of the RLD amplifier 124 and the biasing network 112. The low pass filter 140, the biasing network 112 and the average estimation circuit 116 form a feedback loop between the output 130 of the RLD amplifier 124 and the inverting input 126. The feedback loop sets the voltage at the inverting input 126 to be approximately equal to the voltage VCM_REF (which is applied to the non-inverting input 128). In absence of the low-pass filter 140, the input impedance of ECG path is degraded by the gain of RLD amplifier 124. Since the low-pass filter 140 reduces the gain of the feedback loop at ECG signal band (e.g., 0.5 Hz-250 Hz), the input impedance of ECG path is not degraded and the common-mode rejection ratio (CMRR) is improved.

Figure 2:
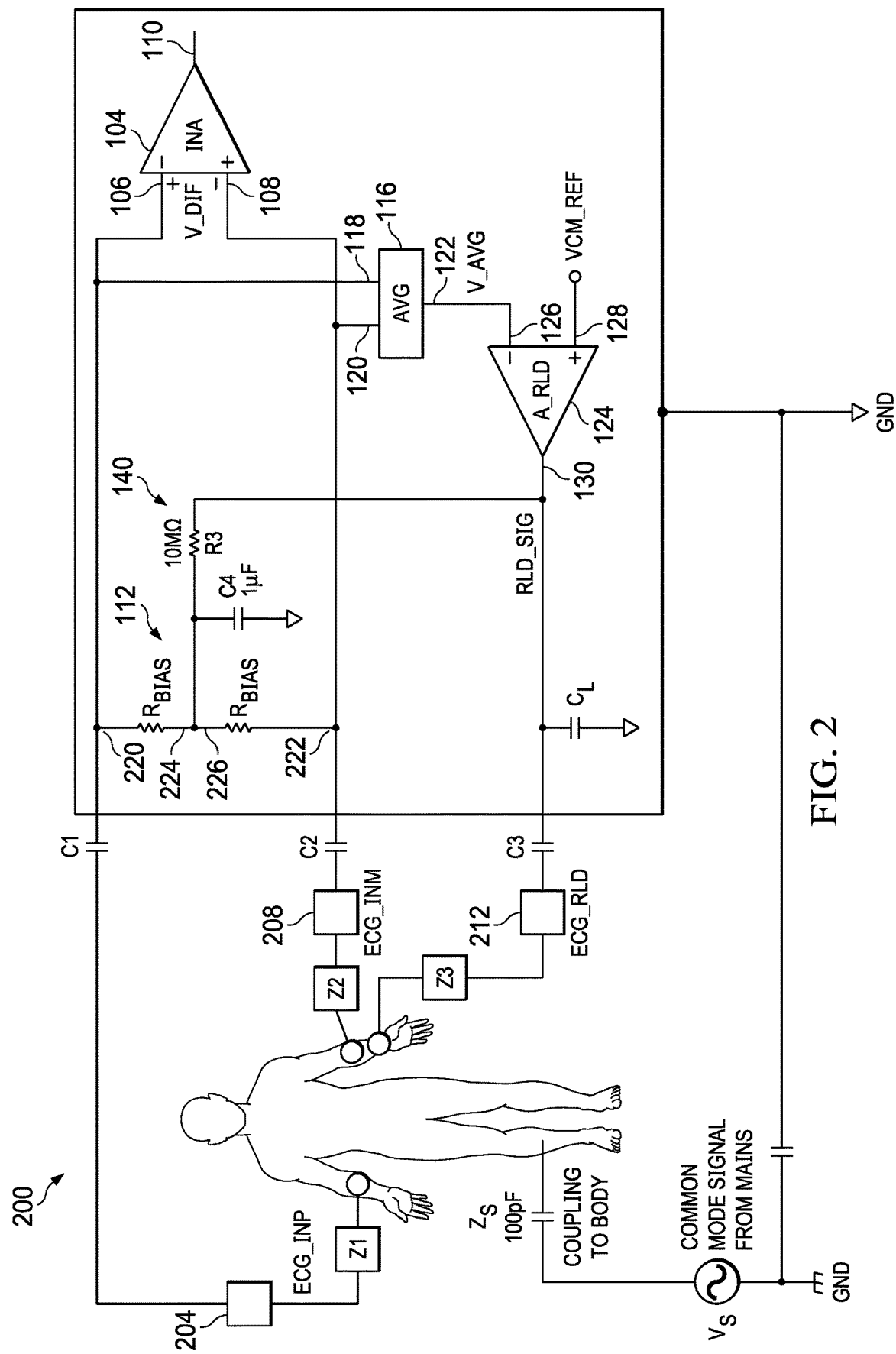
FIG. 2 is a schematic diagram of a system of an example embodiment.

FIG. 2 is a schematic diagram of a system 200 of an example embodiment. The system 200 is adapted to acquire ECG signals from a human body. The system 200 includes a first system input 204 adapted to receive a first ECG signal (ECG_INP) via an electrode Z1. The system 200 includes a second system input 208 adapted to receive a second ECG signal (ECG_INM) via an electrode Z2. The electrodes Z1 and Z2 can be attached to the human body. The system 200 includes a first system output 212 configured to apply an active bias signal, referred to as the right leg drive RLD signal, to the human body. The RLD signal (e.g., 60 Hz) is applied to the human body to suppress common mode signals so that the first and the second ECG signals can be detected and recorded. The RLD signal (ECG_RLD) is applied via an electrode Z3 which can be attached to the human body. The electrodes Z1, Z2, and Z3 can be pads, leads or wearable devices that can be attached to the skin of the human body. In some embodiments, the electrodes Z1 and Z3 can be attached to one arm and the electrode Z2 can be attached to another arm.

The system 200 includes the first amplifier 104 which has the inverting input 106, the non-inverting input 108, and the output 110. A first capacitor C1 is coupled between the first system input 204 and the inverting input 106 of the first amplifier 104, and a second capacitor C2 is coupled between the second system input 208 and the non-inverting input 108 of the first amplifier 104. The capacitors C1 and C2 act as AC coupling capacitors blocking DC offsets from the first and second ECG signals but allowing AC components to pass through (the passed signal referred to as INP and INM, respectively). The first and second ECG signals appear as a differential voltage V_DIFF across the inverting input 106 and the noninverting input 108.

The system 200 includes the biasing network 112 formed by two biasing resistors $R_{BIAS}$ coupled between the inverting and non-inverting inputs 106 and 108 of the first amplifier 104. The first biasing resistor has a first terminal 220 coupled to the inverting input 106 and the second biasing resistor has a first terminal 222 coupled to the non-inverting input 108. The biasing resistors have respective second terminals 224 and 226 which are interconnected to form a resistor node. In an example embodiment, each of the biasing resistors has approximately the same resistance value and/or each biasing resistor has a high resistance (e.g., 200M-ohms).

The system 200 includes the average estimation circuit 116 which has the first input 118 coupled to the inverting input 106 of the first amplifier 104 and has a second input 120 coupled to the non-inverting input 108 of the first amplifier 104. The average estimation circuit 116 provides an average voltage V_AVG value (e.g. an analog voltage value indicative of the average of the voltage at the input 118 and the voltage at the input 120) at the output 122.

In an example embodiment, the average estimation circuit 116 adds the voltages at the input terminals 118 and 120 and determines the average value. The average estimation circuit 116 can, for example, be implemented with a passive resistor network or with an operational amplifier. For example, if Va, Vb, Vc are coupled to the inverting input of an opamp via resistors having a resistance of R, and a feedback resistor Rf is coupled between the inverting input and the output, and the non-inverting input is coupled to ground, Vout=−Rf/R (Va+Vb+Vc). If R=3Rf, Vout=−⅓ (Va+Vb+Vc).

The system 200 includes the RLD amplifier 124. The inverting input 126 of the RLD amplifier 124 is coupled to the output 122 of the average estimation circuit 116 (the output signal referred to as the V_AVG), and the non-inverting input 128 is coupled to receive the reference common-mode voltage VCM_REF. The RLD amplifier 124 applies a gain A_RLD to the difference between the voltages at the input terminals 126 and 128 and provides the RLD signal at the output 130 (RLD_SIG).

A third capacitor C3 is coupled between the system output 212 (ECG_RLD signal) and the output 130 of the RLD amplifier 124 (RLD_SIG). The third capacitor C3 acts as an AC coupling capacitor blocking DC offset from the RLD signal but allowing AC signals to pass through. A load capacitor $C_L$ is coupled between the output 130 of the RLD amplifier 124 and the ground terminal which can be coupled to a common potential (e.g. ground).

The system 200 includes the low-pass filter 140 coupled between the output 130 of the RLD amplifier 124 and the second terminals 224, 226 (i.e., the resistor node) of the first and second biasing resistors. The low-pass filter 140 attenuates selected frequency bands. In some example embodiments, the low-pass filter 140 includes a resistor R3 coupled between the output 130 of the RLD amplifier 124 and the second terminals 224 and 226 of the biasing resistors. In some example embodiments, the low-pass filter 140 includes a capacitor C4 coupled between the second terminals 224, 226 of the biasing resistors and the ground terminal. In an example embodiment, R3 has a high resistance value (e.g., approximately 10 M-ohms) and C4 has a high capacitance value (e.g., approximately 1 uF). As a result, the low pass filter 140 allows only DC current from the output of the RLD amplifier 124 to flow through the biasing resistors but attenuates AC components. In absence of the low-pass filter 140, the output of the RLD amplifier 124 is directly coupled to the second terminals 224, 226 of the biasing resistors, which reduces the input impedance of the ECG path to $R_{BIAS}/A\_RLD$, where A_RLD is the gain of the RLD amplifier 124. The low-pass filter 140 reduces the gain of the feedback loop at ECG signal band to less than 1. Thus the input impedance of ECG path is not degraded and is approximately equal to Rbias. Also there exists a feedback loop with A_RLD gain between the output 130 of the RLD amplifier 124 and the inverting input 126 through C3/Z3 and Z2/C2. The feedback loop causes the voltage at the inverting input 126 to be approximately equal to the voltage at the non-inverting input 128. As a result, the common-mode signal in the human body is sufficiently attenuated.

In addition to the ECG signals which appear as a differential voltage V_DIFF across the inputs 106 and 108 of the first amplifier 104, a common-mode voltage appears at the inputs 106 and 108. The common-mode voltage is normally produced as interference by power lines surrounding the system 200 as well as interference from nearby instruments. In FIG. 2, the common-mode voltage Vcm is produced by an AC line voltage source Vs, which is coupled to the human body via a parasitic capacitance Zs. The parasitic capacitance is approximately 100 pF.

The output Vout of the amplifier 104 can be represented by the equation:

$$Vout=(A1)(V\_DIF+(Acm)(Vcm) \qquad (1)$$

where A1 is the differential gain of system 200 and Acm is the common-mode gain of the system 200. The common-mode voltage Vcm produces an equivalent differential voltage Vcm_dif which can be represented by the equation:

$$Vcm\_dif=Vcm(Z1-Z2)/R_{BIAS}=(Vs/Zs)(Z3/A\_RLD)$$
$$(Z1-Z2)/R_{BIAS} \qquad (2)$$

where Vs is the AC line voltage, Zs is the impedance of the coupling capacitor between the AC line and the human body, and Z1, Z2 and Z3 are the electrode-body contact impedances for electrodes Z1, Z2 and Z3, respectively.

As noted before, the CMRR is defined as the ratio of the differential gain and the common-mode gain. A high CMRR is desired when the small differential signal (i.e., ECG signal) is amplified in the presence of a large common-mode signal produced by the AC line voltage. Since the gain A_RLD of the RLD amplifier 124 is typically high, Vcm_dif is minimized, thus increasing CMRR. Since A_RLD is in the denominator of Eqn (2), Vcm_dif is minimized.

Table I below lists simulation results of the system 200 when coupled to an AC line voltage at 100 Hz (e.g. the common mode signal has a frequency of 100 Hz). The values Z1, Z2 and Z3 are the electrode-body contact impedances for electrodes Z1, Z2 and Z3, respectively. The impedences may vary significantly depending on the location on the skin where the electrode is placed, the moisture of the skin and other factors.

TABLE I

| Z1 (M-ohm) | Z2 (M-ohm) | Z3 (M-ohm) | A_RLD | CMRR (dB) |
| --- | --- | --- | --- | --- |
| 1 | 0 | 1 | 10 | 90.1 |
| 1 | 0 | 1 | 100 | 110.0 |
| 10 | 0 | 10 | 10 | 51.2 |
| 10 | 0 | 10 | 100 | 70.3 |

As shown in Table I, in a first case where Z1=Z3=1 Mohms and Z2=0 ohm, when the gain A_RLD is set to 10 (20 dB), the CMRR=90.1 dB. When the gain A_RLD is increased to 100 (40 dB), CMRR increases to 110.0 dB. In the first case, to indicate Z2 is lower than Z1 and the difference between Z1 and Z2 (i.e., Z1−Z2) is 1 Mohms, Z1 is set at 1 Mohms and Z2 is set at 0 ohms. However, Z2 can be 0.1 Mohms. In other cases, Z1 can be lower than Z2 (e.g., Z2=1 Mohms, Z1=0.1 Mohms.

In a second case where Z1=Z3=10 Mohms and Z2=0 ohm, when the gain A_RLD is set to 10 (20 dB), CMRR=51.2 dB. When the gain A_RLD is increased to 100 (40 dB), CMMR increases to 70.3.

In an example embodiment, the first amplifier 104, the RLD amplifier 124, the average estimation circuit 116, the resistor R3 and the biasing resistors Rbias can be implemented in an integrated circuit (IC).

In this description, the term "couple" may cover connections, communications, or signal paths that enable a functional relationship consistent with this description. For example, if device A provides a signal to control device B to perform an action, then: (a) in a first example, device A is coupled to device B; or (b) in a second example, device A is coupled to device B through intervening component C if intervening component C does not substantially alter the functional relationship between device A and device B, such that device B is controlled by device A via the control signal provided by device A. Also, in this description, a device that is "configured to" perform a task or function may be configured (e.g., programmed and/or hardwired) at a time of manufacturing by a manufacturer to perform the function and/or may be configurable (or reconfigurable) by a user after manufacturing to perform the function and/or other additional or alternative functions. The configuring may be through firmware and/or software programming of the device, through a construction and/or layout of hardware components and interconnections of the device, or a combination thereof. Furthermore, in this description, a circuit or device that includes certain components may instead be adapted to be coupled to those components to form the described circuitry or device. For example, a structure described as including one or more semiconductor elements (such as transistors), one or more passive elements (such as resistors, capacitors and/or inductors), and/or one or more sources (such as voltage and/or current sources) may instead include only the semiconductor elements within a single physical device (e.g., a semiconductor die and/or integrated circuit (IC) package) and may be adapted to be coupled to at least some of the passive elements and/or the sources to form the described structure either at a time of manufacture or after a time of manufacture, such as by an end-user and/or a third party.

As used herein, the terms "terminal", "node", "interconnection", "lead" and "pin" are used interchangeably. Unless specifically stated to the contrary, these terms are generally used to mean an interconnection between or a terminus of a device element, a circuit element, an integrated circuit, a device or other electronics or semiconductor component.

While certain components may be described herein as being of a particular process technology, these components may be exchanged for components of other process technologies. Circuits described herein are reconfigurable to include the replaced components to provide functionality at least partially similar to functionality available before the component replacement. Components shown as resistors, unless otherwise stated, are generally representative of any one or more elements coupled in series and/or parallel to provide an amount of impedance represented by the shown resistor. For example, a resistor or capacitor shown and described herein as a single component may instead be multiple resistors or capacitors, respectively, coupled in series or in parallel between the same two nodes as the single resistor or capacitor. Also, uses of the phrase "ground terminal" in this description include a chassis ground, an Earth ground, a floating ground, a virtual ground, a digital ground, a common ground, and/or any other form of ground connection applicable to, or suitable for, the teachings of this description. Unless otherwise stated, "about", "approximately", or "substantially" preceding a value means +/−10 percent of the stated value.

Modifications are possible in the described embodiments, and other embodiments are possible, within the scope of the claims.

What is claimed is:

1. A system, comprising:
a first amplifier having a first input;
a first resistor having a first terminal coupled to the first input and having a second terminal;
a second resistor having a third terminal coupled to the second input and having a fourth terminal coupled to the second terminal;
an average estimation circuit having a third input coupled to the first input and a fourth input coupled to the second input and an output that is the average voltage of the first input and the second input;
a driver amplifier having a fifth input coupled to the output of the average estimation circuit, a sixth input and an output;
a low-pass filter coupled the output of the driver amplifier and the fourth.

2. The system of claim 1, wherein the low-pass filter is operable to attenuate selected frequency bands from the output of the driver amplifier.

3. The system of claim 1, wherein the first amplifier is operable to apply a gain to the difference between voltages provided at the first and second signals and provide an ECG output.

4. The system of claim 1, further comprising:
a first capacitor coupled between a first system input and the first input of the first amplifier;
a second capacitor coupled between a second system input and the second input of the first amplifier;
a third capacitor coupled between the output of the driver amplifier and a second output.

5. The system of claim 1, wherein the low-pass filter comprises:
a resistor having a first terminal coupled to the output of the driver amplifier and a second terminal coupled to the second terminal of the first resistor; and
a capacitor having a first terminal coupled to the second terminal of the first resistors and a second terminal coupled to a ground terminal.

6. The system of claim 1, wherein the low pass filter is operable to increase the input impedance of the first amplifier.

7. A system, comprising:
a first amplifier having a non-inverting input, an inverting input and an output;
a first capacitor coupled to the non-inverting input of the first amplifier;
a second capacitor coupled the inverting input of the first amplifier;
a first resistor having a first terminal and a second terminal wherein the first terminal is coupled to the non-inverting input of the first amplifier;
a second resistor having a first terminal and a second terminal wherein the first terminal of the second resistor is coupled to the second terminal of the first resistor, and the second terminal of the second resistor is coupled to the inverting input of the first amplifier;
an average estimation circuit having a first input coupled to the non-inverting input of the first amplifier, a second input coupled to the inverting input of the first amplifier, and an output wherein the output is an average a voltage at the non-inverting input and a voltage at the inverting input;
a driver amplifier having an inverting input coupled to the output of the average voltage estimation circuit, a non-inverting input, and an output;
a low-pass filter coupled to the output of the driver amplifier and resistor; and
a third capacitor coupled between the output of the driver amplifier.

8. The system of claim 7, wherein the low-pass filter is operable to allow DC current from the output of the driver amplifier to pass through and apply a DC bias voltage across the non-inverting and inverting inputs of the first amplifier.

9. The system of claim 7, wherein the low-pass filter comprises:
a resistor having a first terminal coupled to the output of the driver amplifier and a second terminal coupled to the first terminal of the second resistor; and
a capacitor having a first terminal coupled to the first terminal of the second resistor and a second terminal coupled to a ground terminal.

10. The system of claim 7, wherein the first amplifier is operable to apply a gain to the difference between voltages provided at the first and second and provide an ECG output.

11. The system of claim 7, wherein the low pass filter is operable to increase the input impedance of the first amplifier.

12. An electrocardiogram (ECG) signal acquisition system, comprising:
- a first amplifier having a non-inverting, an inverting input, and an output;
- a first resistor having a first terminal and a second terminal wherein the first terminal is coupled to the non-inverting input of hte first amplifier;
- a second resistor having a first terminal and a second terminal wherein the first terminal of the second resistor is coupled to the second terminal of the first resistor, and the second terminal of the second resistor is coupled to the inverting input of the first amplifier;
- an average estimation circuit having a first input coupled to the non-inverting input of the first amplifier and a second input coupled to the inverting input of the first amplifier, and an output;
- a driver amplifier having an inverting input coupled to the output of the average estimation circuit, a non-inverting input coupled to receive a first voltage, and an output;
- a low-pass filter having a third resistor coupled between the output of the driver amplifier and the second terminal of the first resistor and having a capacitor coupled to the second terminal of the first resistor and ground; and
- a load capacitor coupled between the output of the driver amplifier and a ground terminal.

13. The system of claim 12, wherein the low pass filter is operable to allow DC current from the output of the driver amplifier to pass through and apply a DC voltage across the non-inverting and inverting inputs of the first amplifier.

14. The system of claim 12, wherein the low-pass filter is operable to attenuate selected frequency bands from the output of the driver amplifier.

15. The system of claim 12, further comprising:
- a first capacitor coupled the non-inverting input of the first amplifier;
- a second capacitor coupled the inverting input of the first amplifier; and
- a third capacitor coupled between the output of the driver amplifier and a second output.

16. The system of claim 12, wherein the low pass filter is operable to increase the input impedance of the first amplifier.

* * * * *